US010380278B2

(12) United States Patent
Thompson et al.

(10) Patent No.: US 10,380,278 B2
(45) Date of Patent: Aug. 13, 2019

(54) VEHICLE CORROSION ANALYZER

(71) Applicant: The Boeing Company, Chicago, IL (US)

(72) Inventors: Richard Joel Thompson, Huntsville, AL (US); Elizabeth Killelea, Huntsville, AL (US); Robert Michael Lawton, Huntsville, AL (US); Kristen Smith Williams, Madison, AL (US)

(73) Assignee: The Boeing Company, Chicago, IL (US)

( * ) Notice: Subject to any disclaimer, the term of this patent is extended or adjusted under 35 U.S.C. 154(b) by 313 days.

(21) Appl. No.: 15/213,116

(22) Filed: Jul. 18, 2016

(65) Prior Publication Data

US 2018/0017481 A1 Jan. 18, 2018

(51) Int. Cl.
*G06G 7/48* (2006.01)
*G06F 17/50* (2006.01)
*G01N 17/00* (2006.01)

(52) U.S. Cl.
CPC ....... *G06F 17/5009* (2013.01); *G01N 17/006* (2013.01)

(58) Field of Classification Search
None
See application file for complete search history.

(56) References Cited

U.S. PATENT DOCUMENTS

| 2008/0234994 A1* | 9/2008 | Goebel | G06F 17/5009 703/7 |
| 2009/0058427 A1* | 3/2009 | Materer | G01N 17/04 324/649 |

OTHER PUBLICATIONS

Bellinger, Nicholas C. et al., "Corrosion Pillowing Stresses in Fuselage Lap Joints", Feb. 1997, AIAA Journal, vol. 35, No. 2, American Institute of Aeronautics and Astronautics. (Year: 1997).*
Liao, Min et al., "Corrosion Risk Assessment of Aircraft Structures", Sep. 2004, Journal of ASTM International, vol. 1, No. 8 (pp. 183, 184, 187-188, 190191, 193, 195-198). (Year: 2004).*
Cole, Ivan S. et al., "Development of a Sensor-Based Learning Approach to Prognostics in Intelligent Vehicle Health Monitoring", 2008, International Conference on Prognostics and Health Management, IEEE. (Year: 2008).*
Hickman, G.A. et. al., "Application of Smart Structures to Aircraft Health Monitoring", Jul. 1991, Journal of Intell. Mater. Syst. and Struct., vol. 2, Technomic Publishing. (Year: 1991).*
Komorowski, J.P. et al., "Research in Corrosion of Ageing Transport Aircraft Structures at SMPL", 2001, Canadian Aeronautics and Space Journal, vol. 47, No. 3. (Year: 2001).*

(Continued)

*Primary Examiner* — Cedric Johnson
(74) *Attorney, Agent, or Firm* — Yee & Associates, P.C.

(57) ABSTRACT

A method and apparatus for analyzing potential corrosion for a vehicle. Potential corrosion surfaces for the vehicle are identified using a model for the vehicle. The corrosion risks are predicted for each of the potential corrosion surfaces. The corrosion risks predicted are aggregated into a group of aggregated corrosion risks for a group of functional design units for the vehicle. A corrosion risk assessment for the vehicle is generated to identify a corrosion risk in the vehicle from the group of aggregated corrosion risks, and to enable a change in the model to reduce the identified corrosion risk.

28 Claims, 13 Drawing Sheets

(56) References Cited

OTHER PUBLICATIONS

Boyer, "New Titanium Applications on the Boeing 777 Airplane," JOM: The Member Journal of the Mineral, Metals & Materials Society (TMS), May 1992, 3 pages.
Froes, Titanium: Physical Metallurgy, Processing, and Applications, ASM International, Materials Park, Ohio, Copyright 2015, 11 pages.

* cited by examiner

VEHICLE CORROSION ANALYZER

BACKGROUND INFORMATION

1. Field

The present disclosure relates generally to vehicles such as aircraft and, in particular, to identifying potential risks of corrosion for the vehicles.

2. Background

Corrosion is a process in which a gradual destruction of materials occurs. This type of corrosion commonly occurs with metals but may also occur with other materials. Corrosion can occur from exposure to moisture in the air, contact between two different types of metals, or through other mechanisms.

In manufacturing of vehicles such as aircraft, corrosion is a challenge with respect to the maintenance and longevity of the aircraft. As part of the manufacturing process, it is desirable to choose materials that reduce potential corrosion risks. The selection of materials, however, may be balanced against other goals such as cost, manufacturability, structural performance, and aerodynamic performance of the aircraft.

Further, with the introduction of composite materials that employ carbon fiber reinforced polymers (CFRPs), the compatibility of these materials with other currently used materials in the aircraft increases the complexity, taking into account the corrosion in the manufacturing of the aircraft. For example, a galvanic potential is present between aluminum and graphite that is found in constant materials. As a result, the use of aluminum, steel, titanium, composite materials, and other materials in the aircraft increases the number of factors that may lead to galvanic corrosion.

Therefore, it would be desirable to have a method and apparatus that take into account at least some of the issues discussed above, as well as other possible issues. For example, it would be desirable to have a method and apparatus that overcome a technical problem with identifying the corrosion risks for the aircraft and other vehicles.

SUMMARY

An embodiment of the present disclosure provides an apparatus. The apparatus is comprised of an extractor, a corrosion predictor, and an aggregator. The extractor is configured to identify potential corrosion surfaces for a vehicle using a model for the vehicle. The corrosion predictor is configured to predict corrosion risks for the potential corrosion surfaces using a group of sources identifying corrosion risks for different types of materials. The aggregator is configured to aggregate the corrosion risks predicted for a group of potential corrosion surfaces into a group of aggregated corrosion risks for a group of functional design units in the vehicle to identify a corrosion risk in the vehicle from the group of aggregated corrosion risks, and to enable a change in the model to reduce the identified corrosion risk.

Another embodiment of the present disclosure provides a corrosion risk analysis system. The corrosion risk analysis system is comprised of an extractor, a corrosion predictor, an aggregator, and a risk analyzer. The extractor is configured to identify material contacts between components in a model for a vehicle during a design phase of the vehicle and identifies potential corrosion contacts for the vehicle using the material contacts and materials present in the structures at the material contacts. The corrosion predictor is configured to predict corrosion risks for the potential corrosion contacts using a group of sources identifying corrosion risks for different types of materials. The aggregator is configured to aggregate the corrosion risks predicted for the group of potential corrosion contacts into a group of aggregated corrosion risks for a group of functional design units in the vehicle. The risk analyzer is configured to generate a corrosion risk assessment for the vehicle using the group of aggregated corrosion risks for the group of functional design units. The corrosion risk assessment is used to identify a corrosion risk in the vehicle from the group of aggregated corrosion risks, and to enable a change in the model to reduce the identified corrosion risk.

Yet another embodiment of the present disclosure provides a method for analyzing potential corrosion for a vehicle. Potential corrosion surfaces for the vehicle are identified using a model for the vehicle. The corrosion risks are predicted for each of the potential corrosion surfaces. The corrosion risks predicted are aggregated into a group of aggregated corrosion risks for a group of functional design units for the vehicle. A corrosion risk assessment for the vehicle is generated to identify a corrosion risk in the vehicle from the group of aggregated corrosion risks, and to enable a change in the model to reduce the identified corrosion risk.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that the use of composite materials in an aircraft increases complexities of potential corrosion. The illustrative embodiments recognize and take into account that currently, in designing the aircraft, the components and materials that are selected in identification of the potential corrosion is performed at a later time.

The illustrative embodiments recognize and take into account that currently, the identification of potential corrosion risks does not occur until design of the aircraft has been completed. The illustrative embodiments recognize and take into account, however, that changing part designs or materials at this late stage may be more expensive and time-consuming than desired.

The illustrative embodiments recognize and take into account that an analysis of the potential corrosion risks may become much more complex with use of the composite materials in addition to metals and metal alloys in the aircraft, as compared to aircraft that do not employ large amounts of the composite materials. The illustrative embodiments recognize and take into account that performing this analysis earlier in the design process may reduce the amount of time and effort for changing the design of the aircraft.

Thus, the illustrative embodiments provide a method and apparatus for analyzing potential corrosion for an aircraft. In one illustrative example, an apparatus is present for analyzing potential corrosion for a vehicle. The apparatus includes an extractor, a corrosion risk predictor, and an aggregator. The extractor is configured to identify potential corrosion surfaces in a model for the vehicle. The corrosion predictor is configured to predict corrosion risks for the potential corrosion surfaces using a group of sources identifying corrosion risks for different types of materials. The aggregator is configured to aggregate the corrosion risks predicted for a group of potential corrosion surfaces into a group of aggregated corrosion risks for a group of functional design units in the vehicle. The group of aggregated corrosion risks enables changing the model to reduce a corrosion risk in the vehicle.

Figure 1:
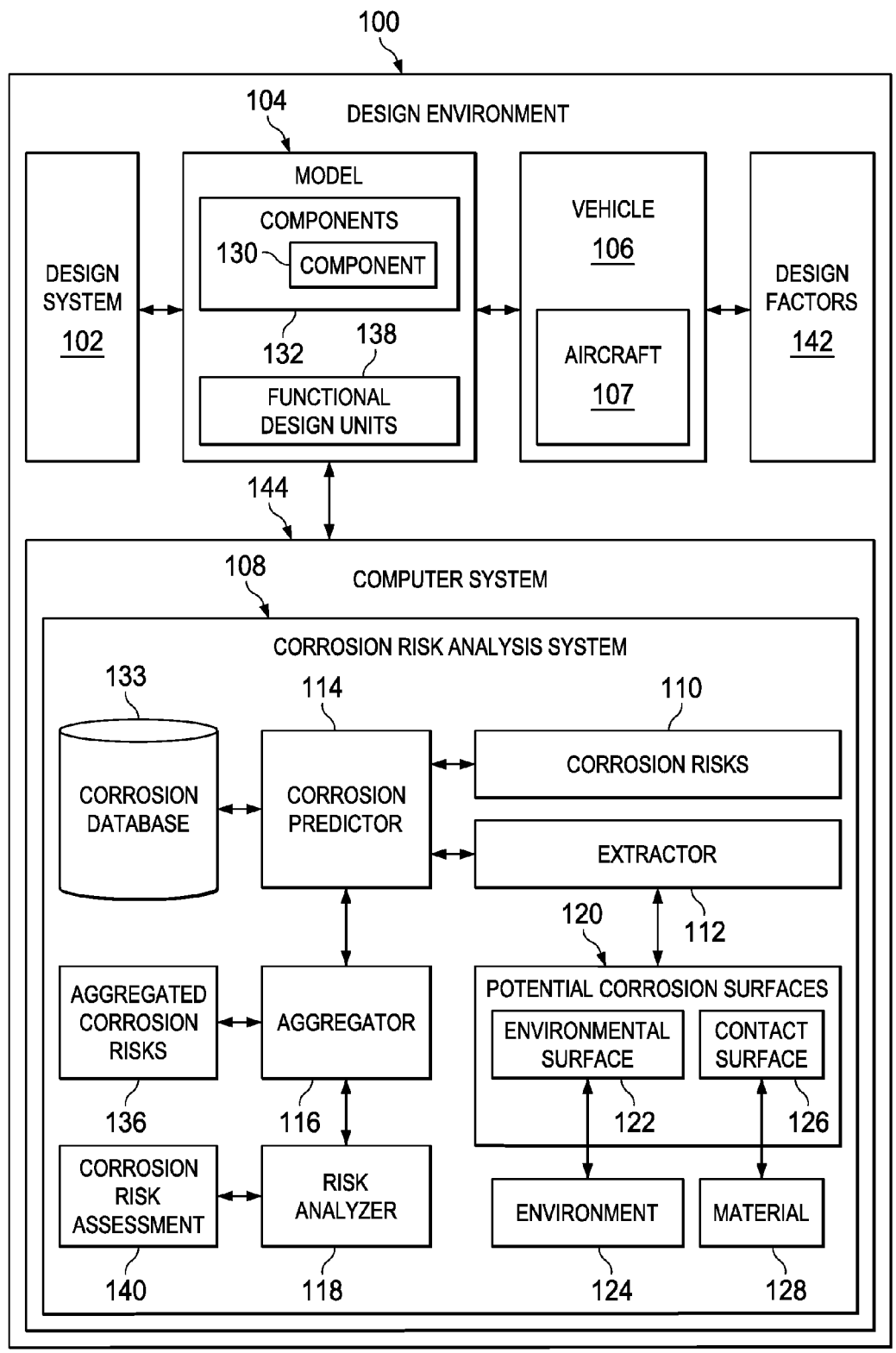
FIG. 1 is an illustration of a block diagram of a design environment in accordance with an illustrative embodiment.

With reference now to the figures and, in particular, with reference to FIG. 1, an illustration of a block diagram of a design environment is depicted in accordance with an illustrative embodiment. As depicted, design environment 100 includes design system 102 which operates to create model 104 for vehicle 106. Design system 102 includes hardware and software. Design system 102 may include, for example, a work station on which computer-aided design (CAD) software runs that is used to create model 104 in the form of a computer-aided design (CAD) model. In another illustrative example, other sources of information may be used to create model 104. For example, parametric geometry may be used in place of or in addition to the computer-aided design (CAD) model.

In this illustrative example, model 104 for vehicle 106 may be a portion or all of vehicle 106. For example, model 104 may contain a part, an assembly, a subassembly, a system, or some other portion of the vehicle 106. Further, vehicle 106 may be an actual vehicle that has been manufactured for production or as a prototype. Vehicle 106 also may be a conceptual vehicle that has not yet been built. As depicted, vehicle 106 is aircraft 107.

In this illustrative example, corrosion risk analysis system 108 is also present in design environment 100. Corrosion risk analysis system 108 operates to identify corrosion risks 110 for vehicle 106. Corrosion risks 110 may be for some or all of vehicle 106.

Corrosion risk analysis system 108 includes a number of different components. As depicted, corrosion risk analysis system 108 includes extractor 112, corrosion predictor 114, aggregator 116, and risk analyzer 118.

As depicted, extractor 112 is configured to identify potential corrosion surfaces 120 for vehicle 106 using model 104 for vehicle 106. In this illustrative example, the identification of potential corrosion surfaces 120 may occur during the design phase of vehicle 106. As depicted, potential corrosion surfaces 120 are selected from at least one of environmental surface 122 that contacts environment 124 or contact surface 126 that contacts material 128.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Environmental surface 122 is a surface on component 130 in components 132 in model 104 for vehicle 106 that is exposed to the environment around vehicle 106. Environmental surface 122 may be an exposed surface on component 130 for vehicle 106. The exposure of environmental surface 122 may be to environmental conditions such as moisture, heat, light, wind, or other types of environmental conditions. Environmental conditions also may include exposure to strikes by foreign object debris during operation of vehicle 106.

Contact surface 126 is a surface on component 130 for vehicle 106 that contacts material 128 for another component in components 132 in vehicle 106. Components 132 are selected from at least one of a part, an assembly, a subassembly, a coating, paint, a sealant, an adhesive, a fastener, a washer, a clip, or some other type of component.

In the illustrative example, corrosion predictor 114 is configured to predict corrosion risks 110 for potential corrosion surfaces 120. As depicted, corrosion risks 110 are selected from at least one of a uniform corrosion, an atmospheric corrosion, an intergranular corrosion, a stress-induced corrosion, a stress-corrosion cracking, a crevice corrosion, a galvanic corrosion, a pitting corrosion, a localized corrosion, a selective leaching, an erosion corrosion, a microbial corrosion, or some other type of corrosion risk of interest or concern.

In the illustrative example, corrosion predictor 114 may use any currently available techniques. In the illustrative example, corrosion predictor 114 uses a group of sources to predict corrosion risks 110 for components 132. In this example, the group of sources is corrosion database 133. As depicted, corrosion database 133 may include entries that identify corrosion risks 110 for different types of materials that may be present in components 132 and potential corrosion surfaces 120.

Corrosion risks 110 may be measured in a number of different ways. For example, corrosion risks 110 may be expressed using one of a corrosion rate, a range of values, a percentage, or some other type of measurement. When corrosion rates are used, the corrosion rates may be compared to each other to identify relative corrosion rates that form corrosion risks 110. In another example, a range of values may be used to indicate a corrosion risk with the lowest value being the lowest corrosion risk for corrosion risks 110, and the highest value being the highest corrosion risk for corrosion risks 110.

As depicted, aggregator 116 is configured to aggregate corrosion risks 110 that are predicted for a group of potential corrosion surfaces 120 into a group of aggregated corrosion risks 136 for a group of functional design units 138 in vehicle 106. In other words, aggregator 116 identifies the group of corrosion risks 110 that are located in a functional design unit in functional design units 138. The group of corrosion risks 110 that is identified for the functional design unit is grouped together to form an aggregated corrosion risk in aggregated corrosion risks 136. This grouping is performed for one or more of the functional design unit in functional design units 138 in which one or more aggregated corrosion risks 136 have been identified.

In this illustrative example, functional design units 138 may take a number of different forms. For example, a functional design unit in the group of functional design units 138 may be selected from at least one of a part, an assembly, a system, and some other type of unit in vehicle 106.

For example, the functional design unit may be selected from one of a fuselage, a wing, a landing gear system, a flap, a horizontal stabilizer, a vertical stabilizer, an engine housing, a cargo deck, a passenger floor, an environmental system, or some other suitable grouping of components. Further, the functional design unit does not have to include components that are all physically in contact with each other. For example, the functional design unit may comprise ribs in the wing or the functional design unit may alternately comprise a single specific rib within the wing. The functional design unit may be selected to encompass one or more components depending on the type of inspection desired.

In this illustrative example, aggregator 116 may identify the aggregated corrosion risk in aggregated corrosion risks 136 for the functional design unit in functional design units 138 based on different rates of corrosion in corrosion risks 110 for the functional design unit. Additionally, aggregator 116 also may generate the aggregated corrosion risk for the functional design unit based on additional factors. These additional factors may include at least one of expected thickness, location, importance of the functional design unit, exposure to the environment, contact area, surface area, geometry, difficulty to reach for maintenance or inspection, or other suitable factors.

Risk analyzer 118 is configured to generate corrosion risk assessment 140 for vehicle 106 using the group of aggregated corrosion risks 136 for the group of functional design units 138. At least one of the group of aggregated corrosion risks 136 or corrosion risk assessment 140 enables changing model 104 to reduce a corrosion risk in vehicle 106. Further, a corrosion risk in vehicle 106 is identified from the group of aggregated corrosion risks 136. Additionally, a change in model 104 is enabled to reduce the identified corrosion risk. As depicted, corrosion risk assessment 140 comprises at least one of the group of aggregated corrosion risks 136, an identification of each of the group of aggregated corrosion risks 136 that is greater than a selected threshold risk, suggested changes to the model 104 that reduce the group of aggregated corrosion risks 136, or some other type of information or suggestions.

Corrosion risk assessment 140 for vehicle 106 may take into account an impact to a group of design factors 142 for vehicle 106. The group of design factors 142 is selected from at least one of corrosion, strength, lift, cost, aerodynamic performance, manufacturability, or some other suitable factor. Thus, corrosion risk assessment 140 for vehicle 106 is feedback for changes to model 104 for vehicle 106.

The different components in corrosion risk analysis system 108 may be implemented in software, hardware, firmware, or a combination thereof. When software is used, the operations performed by the components in corrosion risk analysis system 108 may be implemented in program code configured to run on hardware, such as a processor unit. When firmware is used, the operations performed by corrosion risk analysis system 108 may be implemented in program code and data and stored in persistent memory to run on a processor unit. When hardware is employed, the hardware may include circuits that operate to perform the operations in corrosion risk analysis system 108.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components, excluding a human being. For example, the processes may be implemented as circuits in organic semiconductors.

As depicted, corrosion risk analysis system 108 may be implemented in computer system 144. Computer system 144 is a physical hardware system and includes one or more data processing systems. When more than one data processing system is present, those data processing systems are in communication with each other using a communications medium. The communications medium may be a network.

The data processing systems may be selected from at least one of a computer, a server computer, a tablet, or some other suitable data processing system.

In one illustrative example, one or more technical solutions are present that overcome a technical problem with identifying corrosion risks for aircraft 107 and other vehicles. As a result, one or more technical solutions may provide a technical effect that allows for the identification of corrosion risks 110 and, in particular, aggregated corrosion risks 136 earlier in the process of manufacturing vehicle 106. For example, at least one of aggregated corrosion risks 136 may be identified during certification of vehicle 106, such as aircraft 107. In another illustrative example, aggregated corrosion risks 136 may be identified after configuration of the aircraft but prior to the certification.

Further, the identification also may be made as materials are being selected for different components. Still further, the identification of corrosion risks 110 may be made as part of designing the components themselves. In this manner, the identification of corrosion risks 110 may be performed during many different phases of design of vehicle 106.

In this illustrative example, corrosion risks 110 in the form of corrosion rates are performed on data received from functional design units 138 and at least one of the intersection geometry or other information for functional design units 138. When corrosion rates are calculated, functional design units 138 may have many different corrosion rates. For example, functional design units 138 may be a wing or a rib which may have between ten to thousands of different corrosion rates. Aggregator 116 converts these different rates into a corrosion rate for each of functional design units 138. For example, a single corrosion risk in the form of a corrosion rate for a functional design unit may be identified instead of a thousand different corrosion rates for each functional design unit. Thus, aggregator 116 maps the corrosion rates predicted by corrosion predictor 114 to each functional design unit.

As a result, computer system 144 with corrosion risk analysis system 108 operates as a special purpose computer system in which corrosion risk analysis system 108 in computer system 144 enables identifying aggregated corrosion risks 136 for functional design units 138. In particular, corrosion risk analysis system 108 transforms computer system 144 into a special purpose computer system as compared to currently available general computer systems that do not have corrosion risk analysis system 108.

Figure 2:
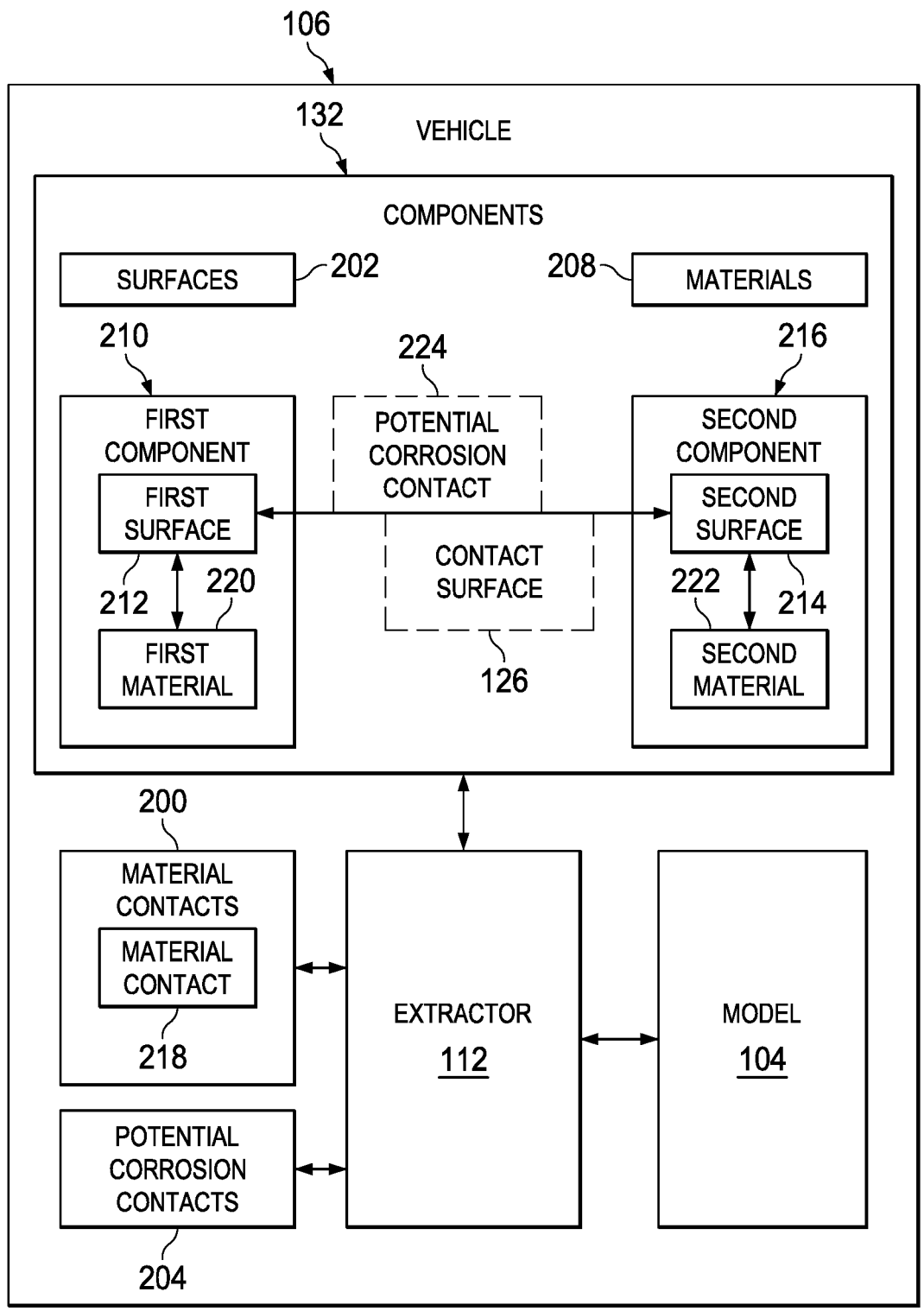
FIG. 2 is an illustration of a block diagram of dataflow for an extractor in accordance with an illustrative embodiment.

With reference to FIG. 2, an illustration of a block diagram of dataflow for an extractor is depicted in accordance with an illustrative embodiment. As depicted, extractor 112 identifies material contacts 200 for surfaces 202 on components 132 in model 104 for vehicle 106 and identifies potential corrosion contacts 204 using material contacts 200 and materials 208 present in components 132 at the material contacts 200. In this illustrative example, potential corrosion contacts 204 are contacts between surfaces on components 132 in which materials 208 and surfaces 202 of components 132 are different types of material from each other rather than being of the same type of material.

In this illustrative example, materials 208 may be included in model 104. In other words, components 132 described in model 104 may be associated with or assigned materials 208 in model 104. In other illustrative examples, materials 208 may be a separate database or other source with identifiers or other information to describe which ones of materials 208 are used for different ones of components 132.

For example, extractor 112 identifies first component 210 in components 132. Extractor 112 identifies first surface 212 on first component 210 that touches second surface 214 on second component 216. In this example, the location where first surface 212 and second surface 214 contact each other is material contact 218 in material contacts 200. Although contact is present between first surface 212 and second surface 214, contact surface 126 may not be potential corrosion contact 224 in potential corrosion contacts 204 depending on the materials in the components at material contact 218.

As depicted, extractor 112 identifies first material 220 in first component 210 at first surface 212. Extractor 112 also identifies second material 222 in second component 216 at second surface 214. If first material 220 is different from second material 222, extractor 112 determines whether potential corrosion contact 224 is present where first surface 212 touches second surface 214. If first material 220 and second material 222 are of the same type, extractor 112 identifies where first surface 212 and second surface 214 touch as a location for potential corrosion contact 224.

Extractor 112 performs this process for each surface on first component 210 and for each component in components 132 for which corrosion risks 110 in FIG. 1 are to be identified. In other words, this process may be performed for some or all of components 132. In this illustrative example, surfaces 202 for components 132 that do not contact surfaces 202 for other components in components 132 are considered environmental surfaces instead of contact surfaces.

Figure 3:
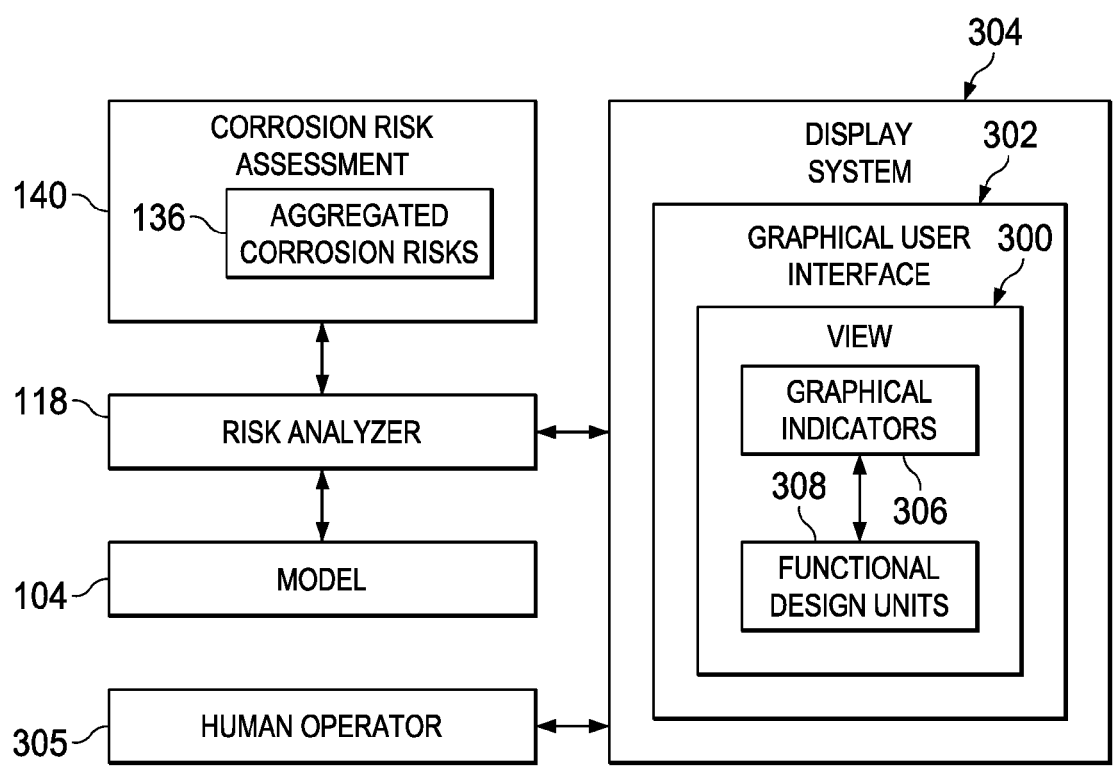
FIG. 3 is an illustration of a block diagram of a model with graphical indications of aggregated corrosion risks on a model for a vehicle in accordance with an illustrative embodiment.

Turning now to FIG. 3, an illustration of a block diagram of a model with graphical indications of aggregated corrosion risks for a vehicle is depicted in accordance with an illustrative embodiment. In this depicted example, risk analyzer 118 is configured to display view 300 of model 104 for vehicle 106 in FIG. 1 in graphical user interface 302 on display system 304 using model 104. View 300 is a visualization of aggregated corrosion risks 136 in corrosion risk assessment 140 that may be seen by human operator 305.

The display of model 104 in view 300 is presented with graphical indicators 306. Graphical indicators 306 indicate a group of aggregated corrosion risks 136 on a group of functional design units 138 displayed in model 104 for vehicle 106.

Display system 304 is a physical hardware system and includes one or more display devices. The display devices may include at least one of a light emitting diode (LED) display, a liquid crystal display (LCD), an organic light emitting diode (OLED) display, or some other suitable device.

As depicted, risk analyzer 118 identifies the group of aggregated corrosion risks 136 identified for model 104. Risk analyzer 118 selects a graphical indicator for each corrosion risk in the group of aggregated corrosion risks 136.

The graphical indicator may be selected to indicate the level of corrosion risk. For example, a high corrosion risk may be assigned red as a color, while a low corrosion risk may be assigned blue as a color. These colors may be displayed on surfaces of the group of functional design units 138 in model 104 on display system 304.

With view 300, human operator 305 may more easily visualize and comprehend aggregated corrosion risks 136 indicated by graphical indicators 306 for functional display units 308 for the design of vehicle 106. In this manner, human operator 305 or some other person may make changes to model 104 to perform at least one of reducing corrosion risks 110 in FIG. 1, aggregated corrosion risks 136 for functional design units 138, or meet some other goal.

The illustration of design environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, vehicle 106 has been described as aircraft 107, but may also take other forms. Vehicle 106 may also be selected from one of a mobile platform, a surface ship, a tank, a personnel carrier, a train, a spacecraft, a satellite, a rocket, a submarine, a bus, an automobile, or some other suitable type of vehicle.

Although color is described as a graphical indicator in FIG. 3, other illustrative examples may use other types of graphical indicators 306. For example, graphical indicators 306 may be selected from at least one of an icon, an image, text, bolding, animation, cross hatching, or other suitable types of graphical indicators in addition to or in place of color.

In yet another illustrative example, corrosion risk analysis system 108 in FIG. 1 may be used during maintenance of vehicle 106. For example, corrosion risk analysis system 108 may be used to design or change designs for components that may be used in maintenance of vehicle 106. This maintenance also includes refurbishment upgrades or other changes to vehicle 106 in which new or different components may be used.

In still another illustrative example, corrosion predictor 114 in FIG. 1 may use other types of sources in addition to or in place of corrosion database 133 in FIG. 1. For example, corrosion predictor 114 may use the group of sources selected from at least one of a lookup table, a knowledge base, artificial intelligence, fuzzy logic, or other sources to predict corrosion risks 110. The group of sources may predict corrosion risks 110, such as when two different materials in two components are in contact with each other or when a material is exposed to the environment. Further, corrosion predictor 114 may also take into account the surface area where contact between the materials occurs. Further, corrosion predictor 114 may use at least one of a physical model, an electrochemical model, or some other suitable type of model to predict corrosion risks 110.

Figure 4:
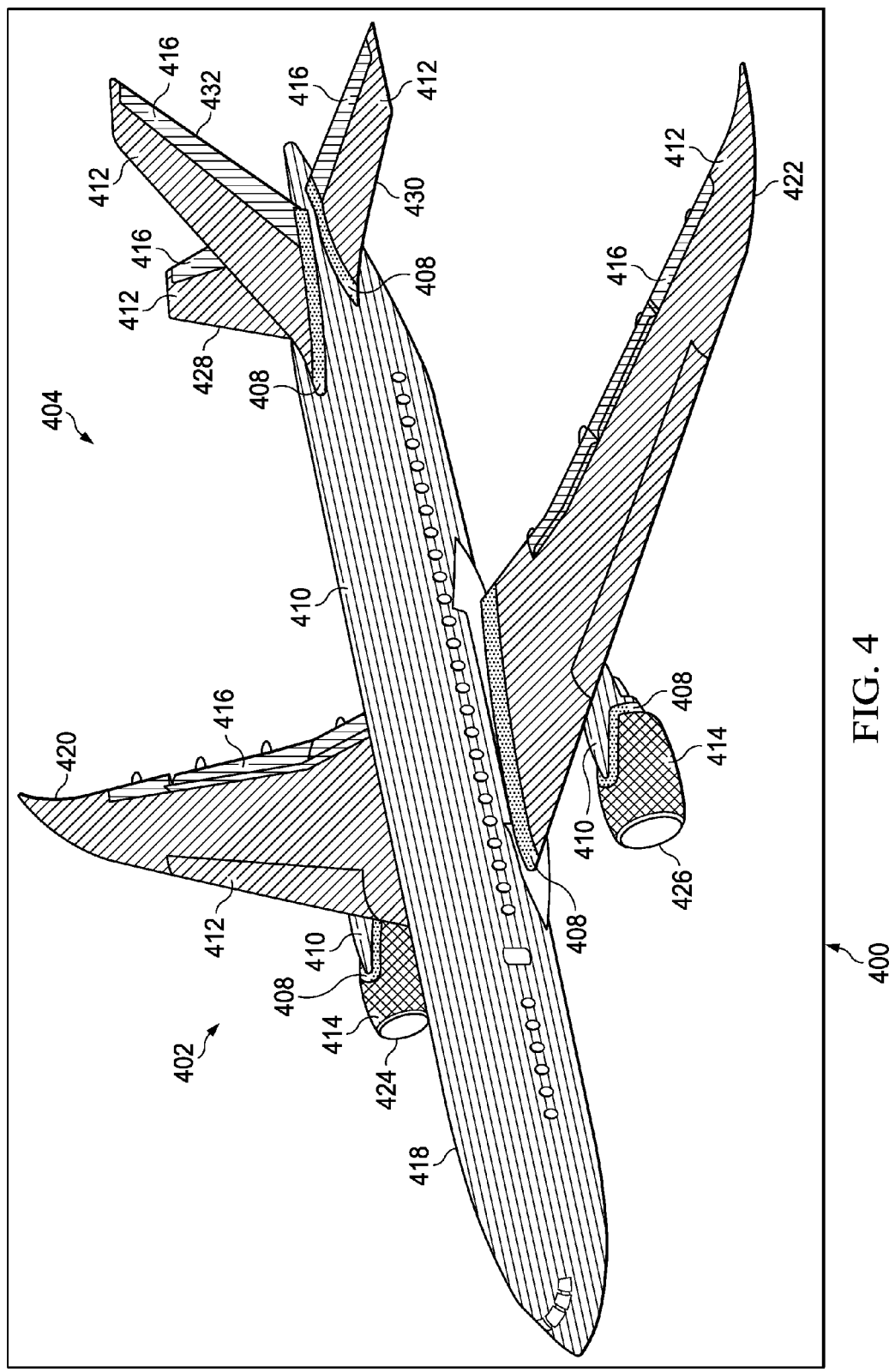
FIG. 4 is an illustration of a view of a corrosion risk assessment for an aircraft in accordance with an illustrative embodiment.

With reference to FIG. 4, an illustration of a view of a corrosion risk assessment for an aircraft is depicted in accordance with an illustrative embodiment. In this illustrative example, view 400 for aircraft 402 is displayed within graphical user interface 404. View 400 is an example of an implementation of view 300 shown in block form in FIG. 3. As depicted, view 400 may be generated by risk analyzer 118 shown in block form in FIG. 1.

As depicted, view 400 is generated from a model for aircraft 402. Additionally, graphical indicators are displayed on aircraft 402 in view 400. As depicted, the graphical indicators include first color 408, second color 410, third color 412, fourth color 414, and fifth color 416. These graphical indicators use color to show aggregated corrosion risks for galvanic corrosion.

In this illustrative example, the colors are displayed to represent aggregated corrosion risks for functional design units in aircraft 402. In this illustrative example, functional design units are fuselage 418, wing 420, wing 422, engine 424, engine 426, horizontal stabilizer 428, horizontal stabilizer 430, and vertical stabilizer 432.

Figure 5:
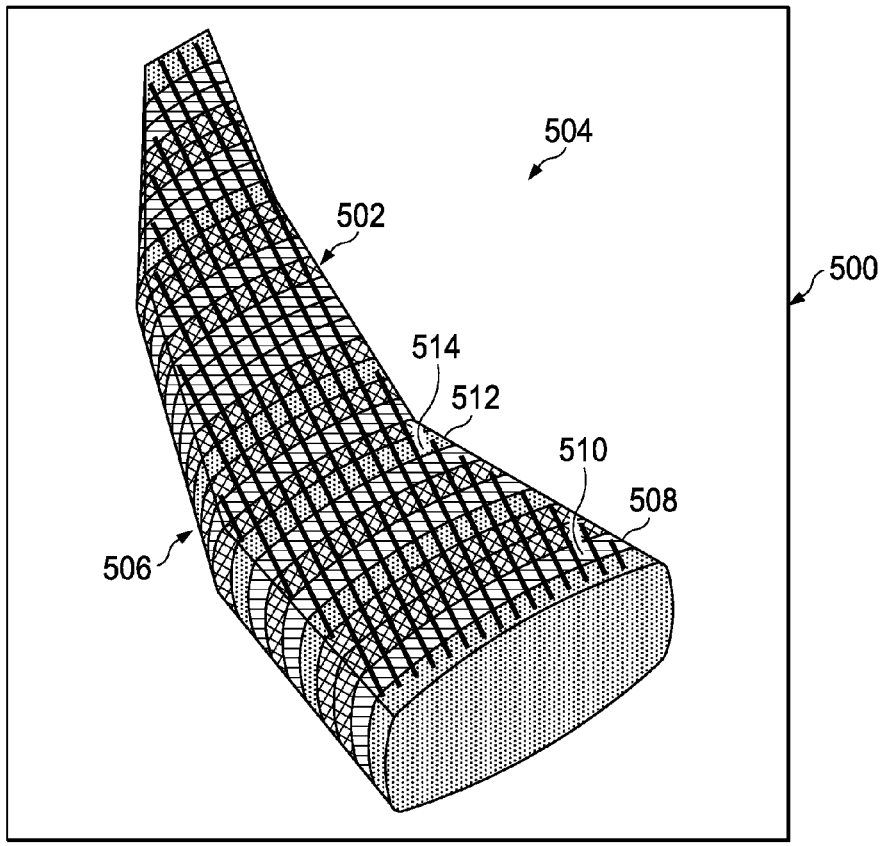
FIG. 5 is an illustration of a view of a corrosion risk assessment for a wing of an aircraft in accordance with an illustrative embodiment.

Turning next to FIG. 5, an illustration of a view of a corrosion risk assessment for a wing of an aircraft is depicted in accordance with an illustrative embodiment. In this illustrative example, view 500 for wing 502 is displayed within graphical user interface 504. View 500 is an example of one implementation of view 300 shown in block form in FIG. 3. As depicted, view 500 may be generated by risk analyzer 118 shown in block form in FIG. 1.

In this illustrative example, view 500 shows structural components 506. As depicted, structural components 506 include spars and ribs for wing 502. In this illustrative example, graphical indicators are shown in the form of color for structural components 506. For example, rib 508 has first color 510 and rib 512 has second color 514. The graphical indicators use colors to show aggregated corrosion risks for pitting corrosion in this particular example.

The illustrations of views of aggregated corrosions risks illustrated in FIG. 4 and FIG. 5 are not meant to limit the manner in which view 300, shown in block form in FIG. 3, may be implemented. For example, other types of views may show other types of corrosion in addition to the aggregated corrosion risks for galvanic corrosion in view 400 in FIG. 4 and the aggregated corrosion risk for pitting corrosion in view 500 in FIG. 5. For example, other views of aggregated corrosion risks in other illustrative examples may show an aggregate corrosion risk, a uniform corrosion, an atmospheric corrosion, an intergranular corrosion, a stress-induced corrosion, a stress-corrosion cracking, a crevice corrosion, a galvanic corrosion, a pitting corrosion, a localized corrosion, a selective leaching, an erosion corrosion, a microbial corrosion, or some other type of corrosion that may be of interest.

Figure 6:
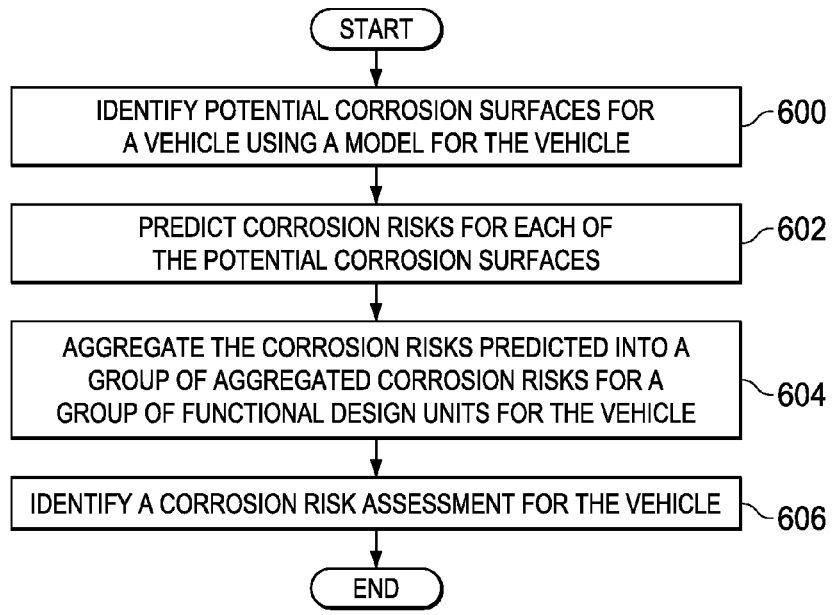
FIG. 6 is an illustration of a flowchart of a process for analyzing potential corrosion for a vehicle in accordance with an illustrative embodiment.

Turning next to FIG. 6, an illustration of a flowchart of a process for analyzing potential corrosion for a vehicle is depicted in accordance with an illustrative embodiment. The process illustrated in FIG. 6 may be implemented in corrosion risk analysis system 108 shown in block form in FIG. 1.

The process begins by identifying potential corrosion surfaces for a vehicle using a model for the vehicle (operation 600). Operation 600 may be implemented in extractor 112 in FIG. 1. The process predicts corrosion risks for each of the potential corrosion surfaces (operation 602). This operation may be implemented in corrosion predictor 114 in FIG. 1. In operation 602, the corrosion risk predicted for each of the potential corrosion surfaces may be selected from at least one of a uniform corrosion, an atmospheric corrosion, an intergranular corrosion, a stress-induced corrosion, stress-corrosion cracking, a crevice corrosion, a galvanic corrosion, a pitting corrosion, a localized corrosion, a selective leaching, an erosion corrosion, a microbial corrosion. Each of these corrosion risks may be predicted using information from a single source or from multiple sources.

Next, the process aggregates the corrosion risks predicted into a group of aggregated corrosion risks for a group of functional design units for the vehicle (operation 604). As depicted, operation 604 may be implemented in aggregator 116 in FIG. 1.

The process then identifies a corrosion risk assessment for the vehicle (operation 606). This operation may be implemented in risk analyzer 118 in FIG. 1. The process terminates thereafter. This process enables changing the model to reduce a corrosion risk in the vehicle.

Figure 7:
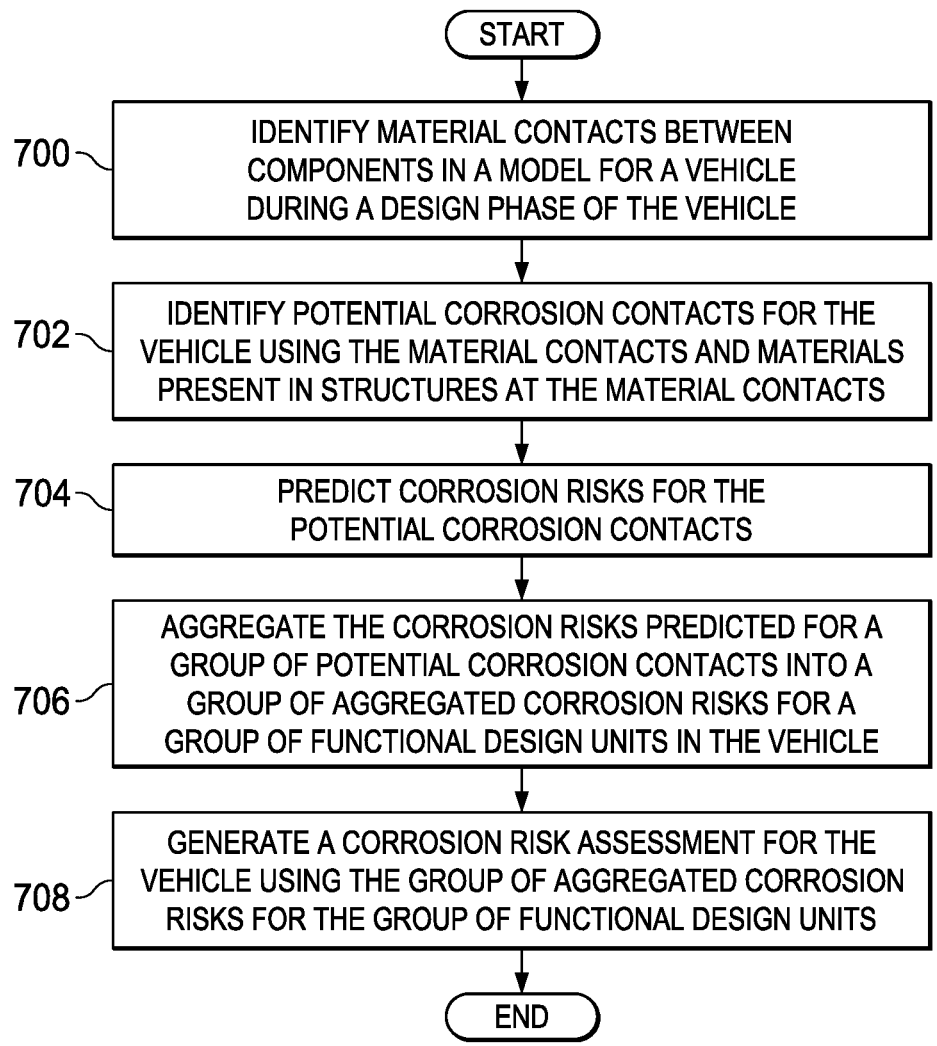
FIG. 7 is another illustration of a flowchart of a process for analyzing potential corrosion for a vehicle in accordance with an illustrative embodiment.

With reference to FIG. 7, another illustration of a flowchart of a process for analyzing potential corrosion for a vehicle is depicted in accordance with an illustrative embodiment. The process illustrated in FIG. 7 may be implemented in corrosion risk analysis system 108 shown in block form in FIG. 1.

The process begins by identifying material contacts between components in a model for a vehicle during a design phase of the vehicle (operation 700). This operation may be implemented in extractor 112 in FIG. 1. The process then identifies potential corrosion contacts for the vehicle using the material contacts and materials present in structures at the material contacts (operation 702). This operation may be implemented in extractor 112 in FIG. 1.

Next, the process predicts corrosion risks for the potential corrosion contacts (operation 704). This operation may be implemented in corrosion predictor 114 in FIG. 1. The process then aggregates the corrosion risks predicted for a group of potential corrosion contacts into a group of aggregated corrosion risks for a group of functional design units in the vehicle (operation 706). As depicted, operation 706 may be implemented in aggregator 116 in FIG. 1. Next, the process generates a corrosion risk assessment for the vehicle using the group of aggregated corrosion risks for the group of functional design units (operation 708) with the process terminating thereafter. This operation may be implemented in risk analyzer 118 in FIG. 1. The corrosion risk assessment enables changing the model to change the design of the vehicle such that a corrosion risk in the vehicle is reduced.

Figure 8:
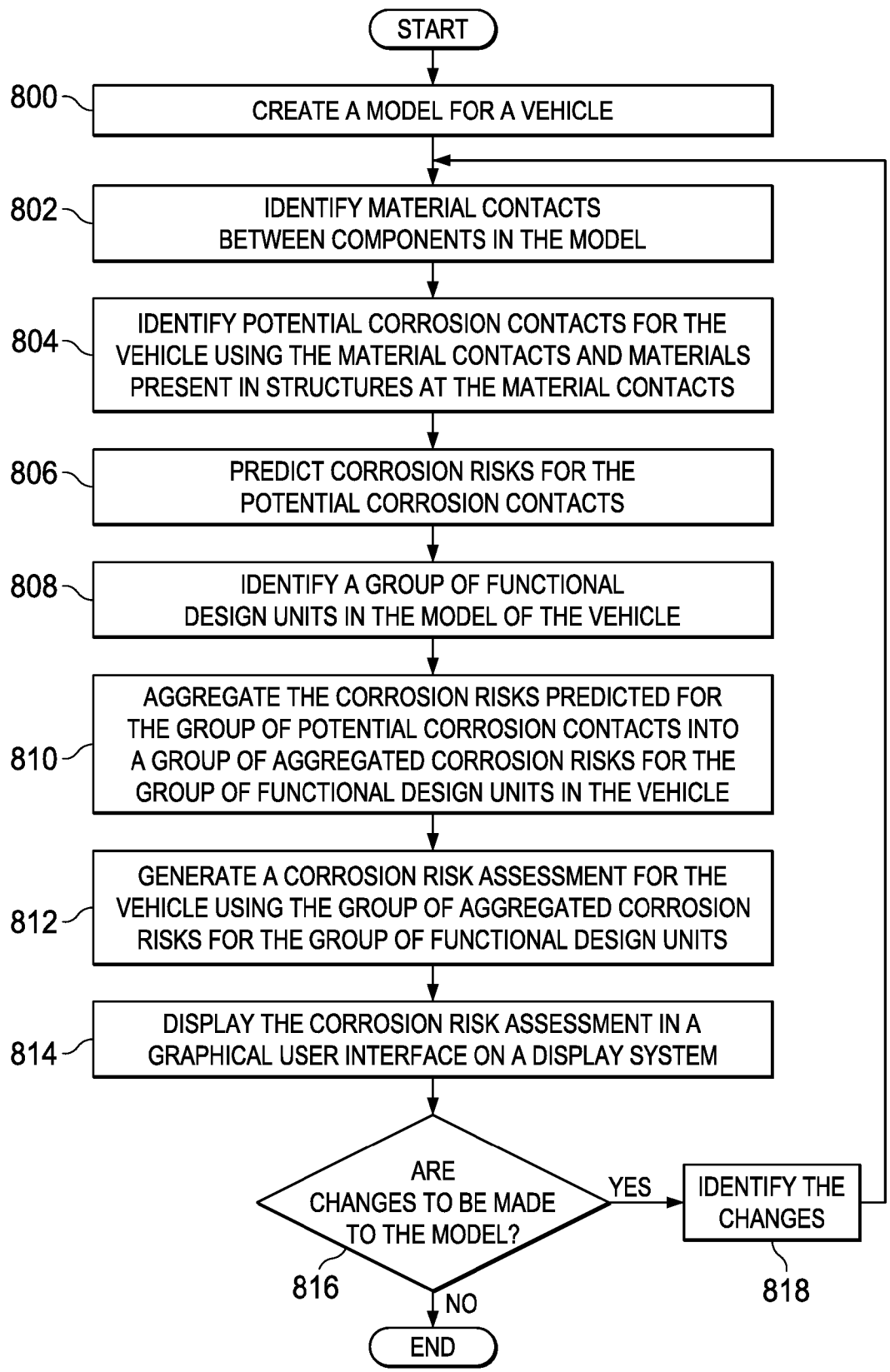
FIG. 8 is an illustration of a flowchart of a process for designing a vehicle in accordance with an illustrative embodiment.

With reference next to FIG. 8, an illustration of a flowchart of a process for designing a vehicle is depicted in accordance with an illustrative embodiment. The process begins by creating a model for a vehicle (operation 800). This model may be for a portion or all of the vehicle.

The process identifies material contacts between components in the model (operation 802). The process then identifies potential corrosion contacts for the vehicle using the material contacts and materials present in structures at the material contacts (operation 804). The process predicts corrosion risks for the potential corrosion contacts (operation 806).

Next, the process identifies a group of functional design units in the model of the vehicle (operation 808). The process then aggregates the corrosion risks predicted for the group of potential corrosion contacts into a group of aggregated corrosion risks for the group of functional design units in the vehicle (operation 810).

Next, the process generates a corrosion risk assessment for the vehicle using the group of aggregated corrosion risks for the group of functional design units (812). The process then displays the corrosion risk assessment in a graphical user interface on a display system (operation 814).

A determination is made as to whether changes are to be made to the model (operation 816). If changes are to be made to the model, the process identifies the changes (operation 818) with the process returning to operation 802 as described above.

These changes to the model may be made to existing functional design units. For example, materials and components in existing functional design units may be changed, new components may be added, components may be removed, or other changes may be made.

In other illustrative examples, the changes may be the creation of components that form one or more new functional design units. For example, the design of the vehicle may be performed incrementally with corrosion risk assessments being made at different stages in the design of the vehicle. In another illustrative example, the changes may remove a functional design unit.

With reference again to operation 816, if changes are not to be made to the model, the process terminates. In this manner, the changes to the design of the vehicle may be made during different times in the life cycle of the vehicle.

This type of analysis and changes may also be made during the use of the vehicle. For example, the analysis may be made using models of vehicles already manufactured and in use. In another illustrative example, the analysis and changes may be made to parts or components for refurbishing or upgrading the vehicles during maintenance of the vehicles.

Figure 9:
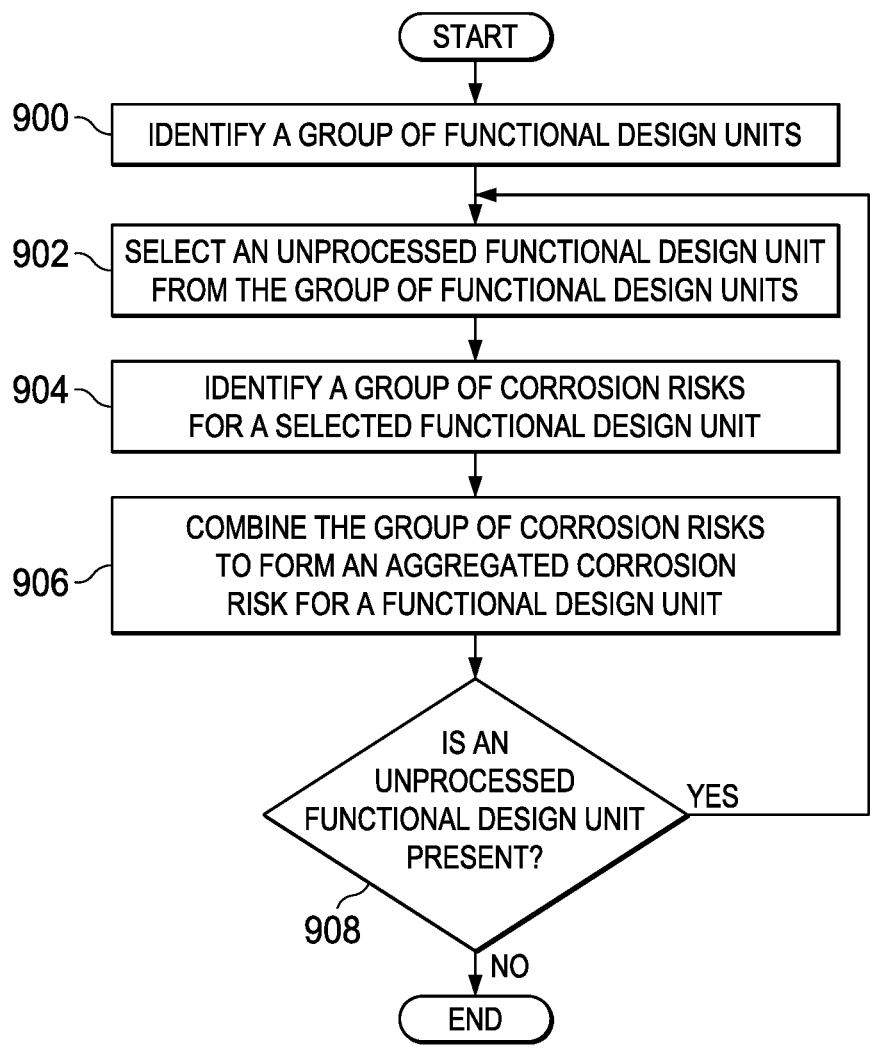
FIG. 9 is an illustration of a flowchart of a process for aggregating corrosion risks in accordance with an illustrative embodiment.

With reference now to FIG. 9, an illustration of a flowchart of a process for aggregating corrosion risks is depicted in accordance with an illustrative embodiment. The process illustrated in FIG. 9 may be implemented in aggregator 116 in FIG. 1.

The process begins by identifying a group of functional design units (operation 900). The process then selects an unprocessed functional design unit from the group of functional design units (operation 902).

Next, the process identifies a group of corrosion risks for a selected functional design unit (operation 904). The process then combines the group of corrosion risks to form an aggregated corrosion risk for a functional design unit (operation 906).

In this illustrative example, a combination of the corrosion risks in operation 906 may be performed in a number of different ways. For example, the group of corrosion risks may be averaged to form an aggregate corrosion risk for the functional design unit. In another example, individual corrosion risks may be weighed based on factors such as thickness, accessibility for maintenance, accessibility for inspection, aerodynamic importance of the functional design unit, or other suitable factors.

In yet another illustrative example, corrosion rates on an object may be compared to a policy. The policy is one or more rules. A corrosion rate that does not meet the policy may be flagged, and a graphical indicator may be displayed to indicate that the corrosion rate does not meet one or more rules in the policy.

For example, the combination may be based on various user specifications. In one example, the combination may be to find a maximum risk anywhere in the vehicle. In this case, a supremum or a maximum analysis is performed using the largest risk available on each functional design unit to calculate the corrosion risk.

In another example, the specification may desire weighting the different corrosion rates and combining the weighted corrosion rates with other information available. For example, one surface on the aircraft may have an undesired galvanic corrosion rate, but the structure on which the surface is located may have a thickness such that the total degradation is small enough over the lifespan of the aircraft such that the corrosion rate is acceptable. In this case, the corrosion risk should be considered smaller as compared to the same surface with a thinner structure.

Thereafter, a determination is made as to whether an unprocessed functional design unit is present (operation 908). If an additional unprocessed functional design unit is present, the process returns to operation 902. Otherwise, the process terminates.

Figure 10:
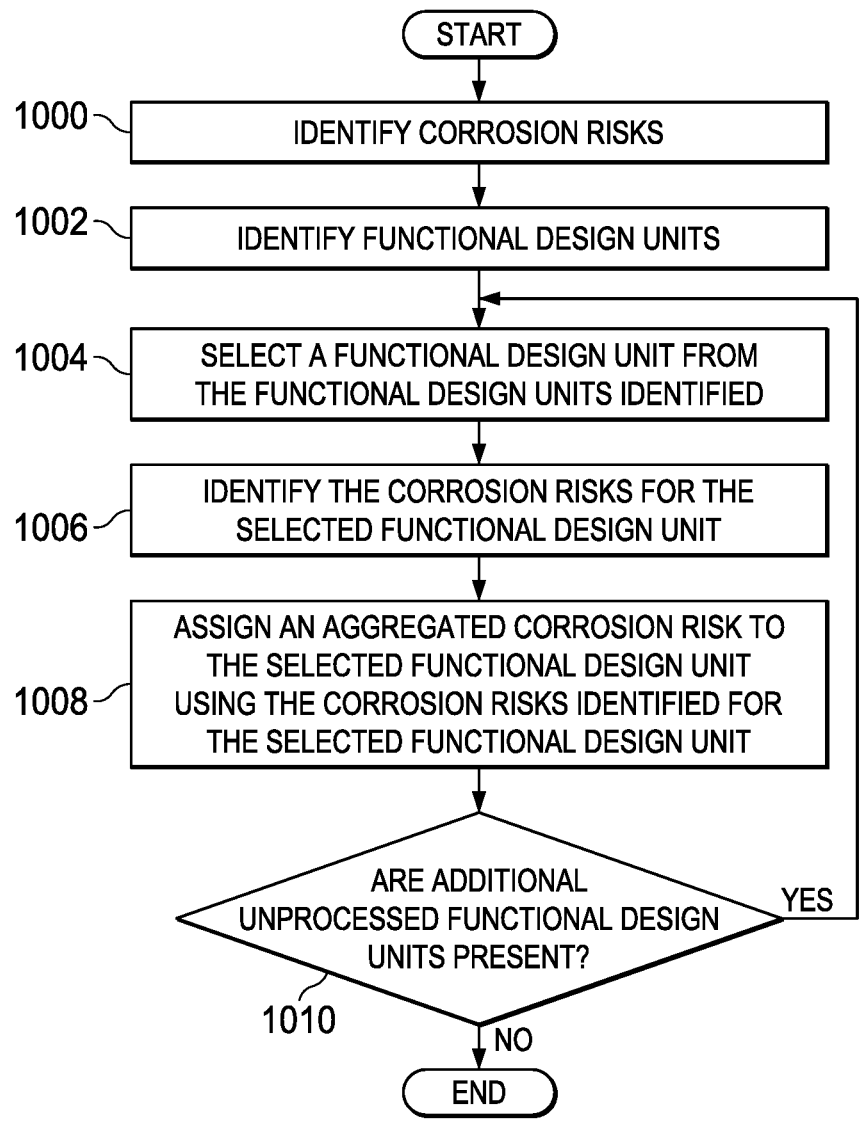
FIG. 10 is another illustration of a flowchart of a process for aggregating corrosion risks in accordance with an illustrative embodiment.

With reference to FIG. 10, another illustration of a flowchart of a process for aggregating corrosion risks is depicted in accordance with an illustrative embodiment. The process illustrated in FIG. 10 may be implemented in aggregator 116 in FIG. 1.

The process begins by identifying corrosion risks (operation 1000). The corrosion risks may be received from corrosion predictor 114 in FIG. 1. These corrosion risks may be, for example, corrosion rates. The process also identifies functional design units (operation 1002).

The process then selects a functional design unit from the functional design units identified (operation 1004). The process identifies the corrosion risks for the selected functional design unit (operation 1006). The process then assigns an aggregated corrosion risk to the selected functional design unit using the corrosion risks identified for the selected functional design unit (operation 1008).

In operation 1008, the aggregated corrosion risk may be assigned in a number of different ways. For example, a value for an overall corrosion risk may be identified from all of the different corrosion risks for the functional design unit. An average corrosion risk may be calculated.

When a value is calculated, other functions other than an arithmetic average may be used. For example, a weighted average may be employed in which different corrosion risks are weighted and then averaged. The weighting may be based on various factors such as location, exposure to environment, thickness of material, type of the material, and other factors relating to the functional design unit.

In yet another illustrative example, operation 1008 may be implemented as a binary value in which the aggregated corrosion risk for the functional design unit is an indication of whether the corrosion risk is "acceptable" or "unacceptable". This identification may be made using a policy that contains one or more rules. For example, the corrosion risks for the functional design unit may be averaged and compared to a threshold value.

In still another illustrative example, rules may be used to determine whether individual corrosion risks within the functional design unit exceed a threshold value. In this particular example, if any corrosion risk exceeds the threshold, the aggregate corrosion risk is assigned to indicate that the corrosion risk for the functional design unit is unacceptable. Additionally, more than two categories may be present. For example, the categories may be "acceptable", "marginally acceptable", and "unacceptable".

Also, a maximum risk assignment may be made in aggregating the corrosion risks for the functional design units. For example, the largest corrosion risk for the different corrosion risks identified for a functional design unit is assigned to the functional design unit as the aggregated corrosion risk.

A determination is made as to whether additional unprocessed functional design units are present (operation 1010). If additional unprocessed functional design units are present, the process returns to operation 1004. Otherwise, the process terminates.

Figure 11:
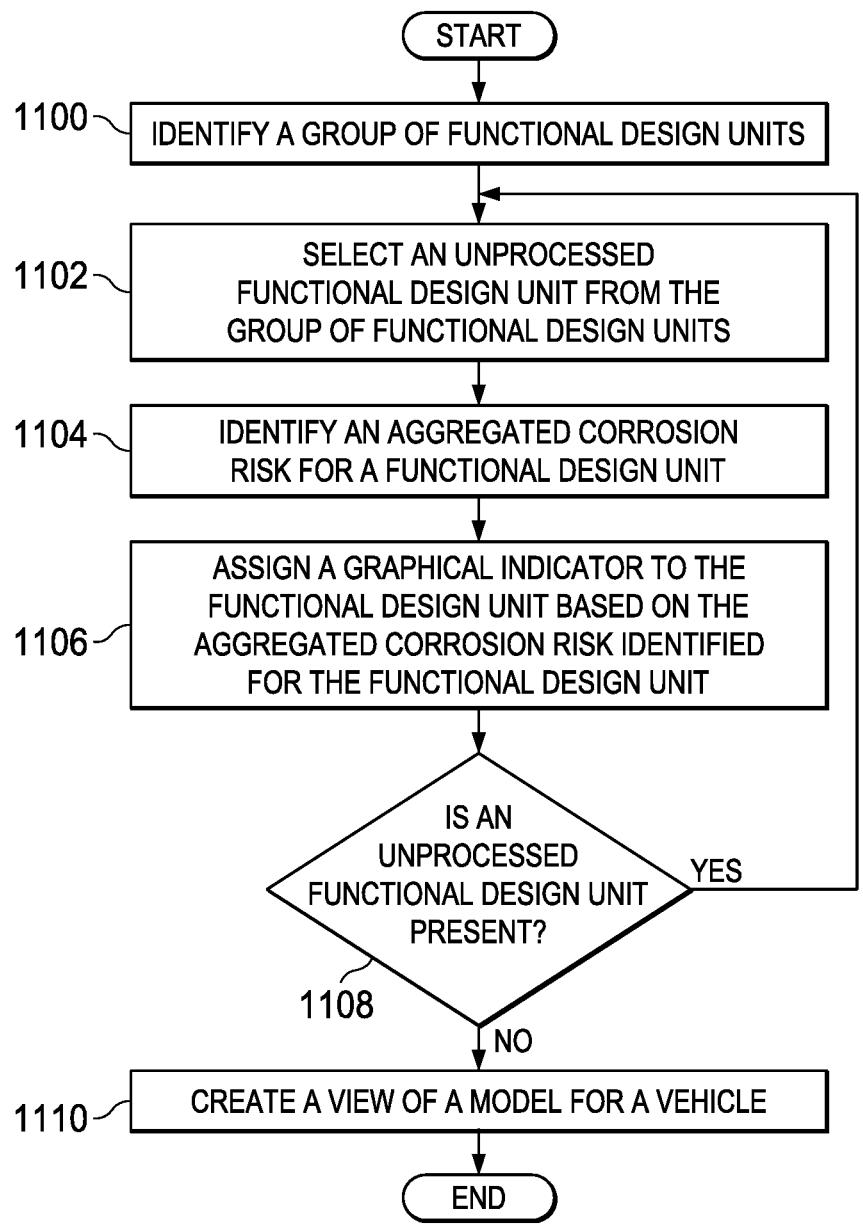
FIG. 11 is an illustration of a flowchart of a process for generating a view of aggregated corrosion risks in accordance with an illustrative embodiment.

Turning next to FIG. 11, an illustration of a flowchart of a process for generating a view of aggregated corrosion risks is depicted in accordance with an illustrative embodiment. The process illustrated in FIG. 11 may be implemented in risk analyzer 118 in FIG. 1.

The process begins by identifying a group of functional design units (operation 1100). The process then selects an unprocessed functional design unit from the group of functional design units (operation 1102).

Next, the process identifies an aggregated corrosion risk for a functional design unit (operation 1104). The process then assigns a graphical indicator to the functional design unit based on the aggregated corrosion risk identified for the functional design unit (1106).

A determination is made as to whether an unprocessed functional design unit is present (operation 1108). If an additional unprocessed functional design unit is present, the process returns to operation 1102.

Otherwise, the process creates a view of a model for a vehicle (1110) with the process terminating thereafter. As depicted, the view may be a portion or all of the vehicle depending on the contents of the model.

The process in FIG. 11 may be performed for individual corrosion risks in addition to or in place of the aggregate corrosion risks. The individual corrosion risks may be displayed in the view with the aggregate corrosion risks so that particular locations on the functional design unit may be examined for potential changes.

For example, a color may be used to indicate the aggregate corrosion risk for the functional design unit while other types of graphical indicators, such as numbers or icons, may be used to identify corrosion risks at particular locations where two components have contact. The overall color may draw attention to functional design units that may have higher or the highest corrosion risks. The identification of individual corrosion risks on the functional design unit may be used to consider changes to the design of the functional design unit. For example, a coating may be added, a finish may be changed, a material may be changed for one or more of the components that have surfaces that contact each other, the area of contact between the components may be changed, or some other modification may be made to reduce the corrosion risk at that location and for the functional design unit overall.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step.

For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 12:
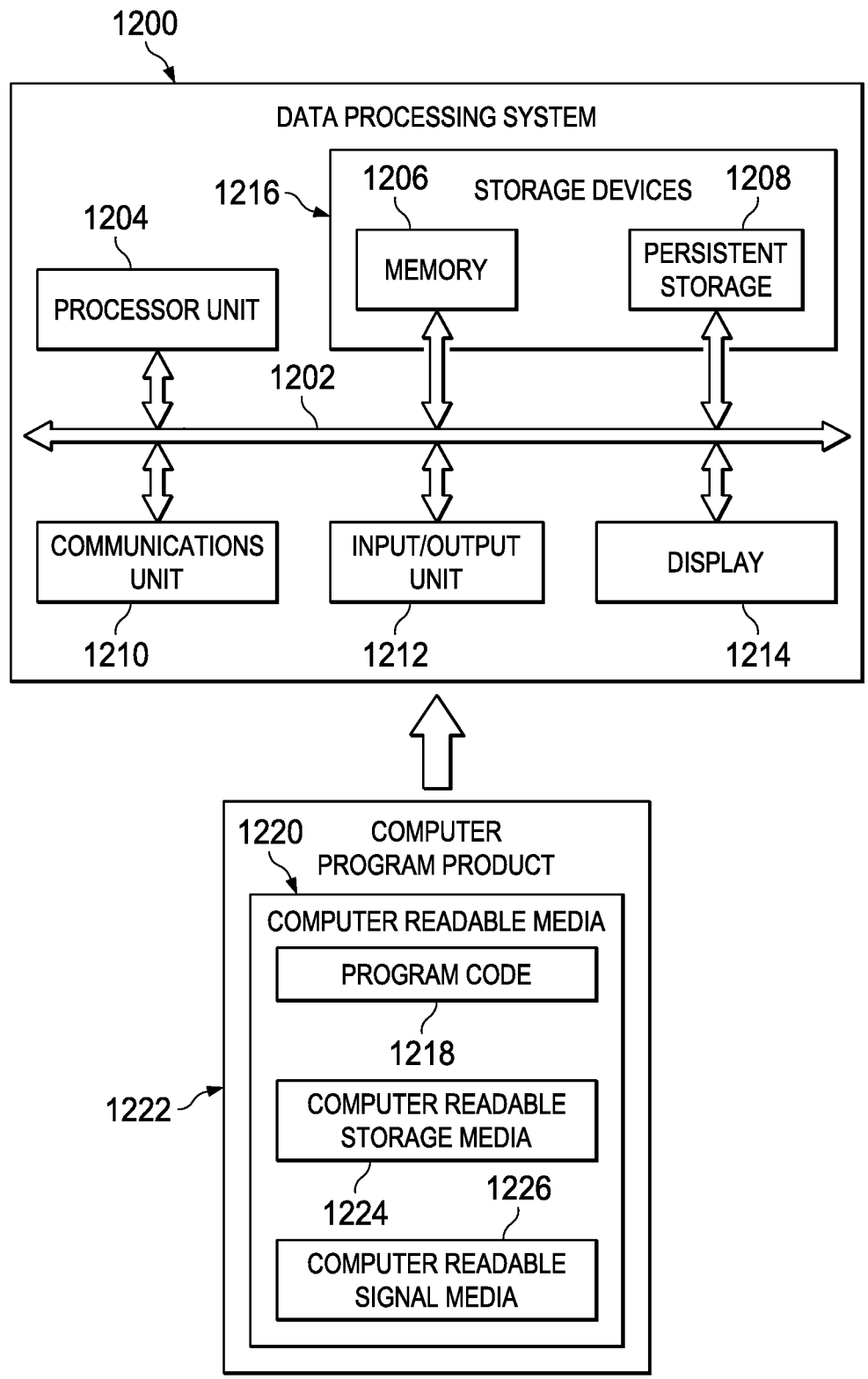
FIG. 12 is an illustration of a block diagram of a data processing system in accordance with an illustrative embodiment.

Turning now to FIG. 12, an illustration of a block diagram of a data processing system is depicted in accordance with an illustrative embodiment. Data processing system 1200 may be used to implement computer system 144 in FIG. 1. In this illustrative example, data processing system 1200 includes communications framework 1202, which provides communications between processor unit 1204, memory 1206, persistent storage 1208, communications unit 1210, input/output (I/O) unit 1212, and display 1214. In this example, communications framework 1202 may take the form of a bus system.

Processor unit 1204 serves to execute instructions for software that may be loaded into memory 1206. Processor unit 1204 may be a number of processors, a multi-processor core, or some other type of processor, depending on the particular implementation.

Memory 1206 and persistent storage 1208 are examples of storage devices 1216. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1216 may also be referred to as computer readable storage devices in these illustrative examples. Memory 1206, in these examples, may be, for example, a random access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a solid state hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these illustrative examples, provides for communications with other data processing systems or devices. In these illustrative examples, communications unit 1210 is a network interface card.

Input/output unit 1212 allows for input and output of data with other devices that may be connected to data processing system 1200. For example, input/output unit 1212 may provide a connection for user input through at least one of a keyboard, a mouse, or some other suitable input device. Further, input/output unit 1212 may send output to a printer. Display 1214 provides a mechanism to display information to a user.

Instructions for at least one of the operating system, applications, or programs may be located in storage devices 1216, which are in communication with processor unit 1204 through communications framework 1202. The processes of the different embodiments may be performed by processor unit 1204 using computer-implemented instructions, which may be located in a memory, such as memory 1206.

These instructions are referred to as program code, computer usable program code, or computer readable program code that may be read and executed by a processor in processor unit 1204. The program code in the different embodiments may be embodied on different physical or computer readable storage media, such as memory 1206 or persistent storage 1208.

Program code 1218 is located in a functional form on computer readable media 1220 that is selectively removable and may be loaded onto or transferred to data processing system 1200 for execution by processor unit 1204. Program code 1218 and computer readable media 1220 form computer program product 1222 in these illustrative examples. In one example, computer readable media 1220 may be computer readable storage media 1224 or computer readable signal media 1226. In these illustrative examples, computer readable storage media 1224 is a physical or tangible storage device used to store program code 1218 rather than a medium that propagates or transmits program code 1218.

Alternatively, program code 1218 may be transferred to data processing system 1200 using computer readable signal media 1226. Computer readable signal media 1226 may be, for example, a propagated data signal containing program code 1218. For example, computer readable signal media 1226 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1200 are not meant to provide architectural limitations to the manner in which different embodiments may be implemented. The different illustrative embodiments may be implemented in a data processing system including components in addition to or in place of those illustrated for data processing system 1200. Other components shown in FIG. 12 can be varied from the illustrative examples shown. The different embodiments may be implemented using any hardware device or system capable of running program code 1218.

Figure 13:
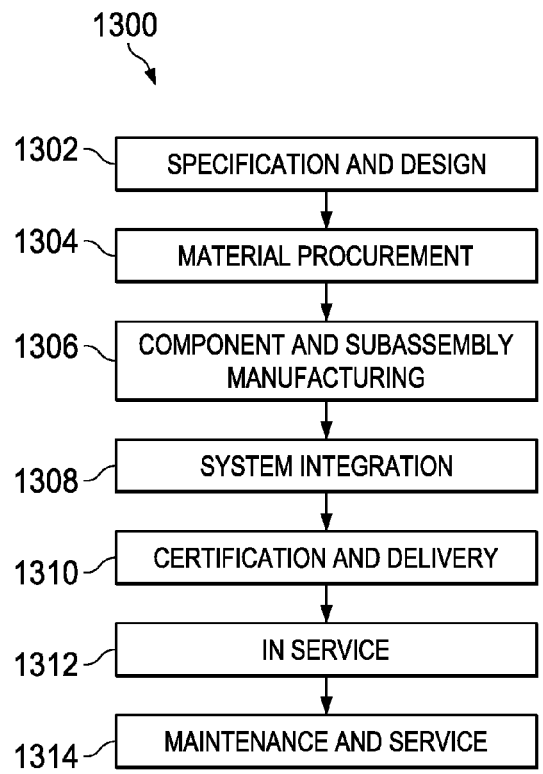
FIG. 13 is an illustration of a block diagram of an aircraft manufacturing and service method in accordance with an illustrative embodiment.
Figure 14:
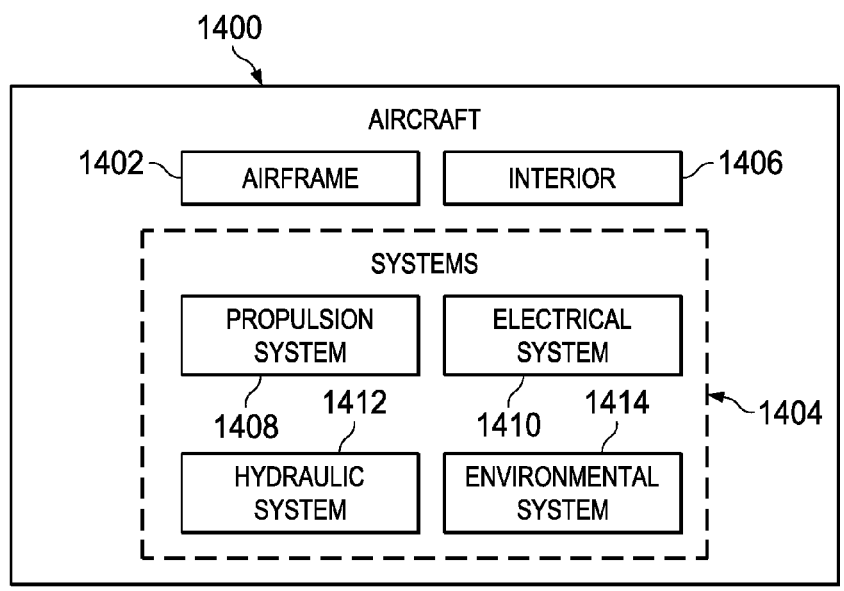
FIG. 14 is an illustration of a block diagram of an aircraft in which an illustrative embodiment may be implemented.

The illustrative embodiments of the present disclosure may be described in the context of aircraft manufacturing and service method 1300 as shown in FIG. 13 and aircraft 1400 as shown in FIG. 14. Turning first to FIG. 13, an illustration of a block diagram of an aircraft manufacturing and service method is depicted in accordance with an illustrative embodiment. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 takes place. Thereafter, aircraft 1400 may go through certification and delivery 1310 in order to be placed in service 1312. While in service 1312 by a customer, aircraft 1400 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of a block diagram of an aircraft is depicted in which an illustrative embodiment may be implemented. In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. In one illustrative example, components or subassemblies produced in component and subassembly manufacturing 1306 in FIG. 13 may be fabricated or manufactured in a manner similar to components or subassemblies produced while aircraft 1400 is in service 1312 in FIG. 13. As yet another example, one or more apparatus embodiments, method embodiments, or a combination thereof may be utilized during production stages, such as component and subassembly manufacturing 1306 and system integration 1308 in FIG. 13.

One or more apparatus embodiments, method embodiments, or a combination thereof may be utilized while aircraft 1400 is in service 1312, during maintenance and service 1314 in FIG. 13, or both. The use of a number of the different illustrative embodiments may substantially expedite the assembly of aircraft 1400, reduce the cost of aircraft 1400, or both expedite the assembly of aircraft 1400 and reduce the cost of aircraft 1400.

Figure 15:
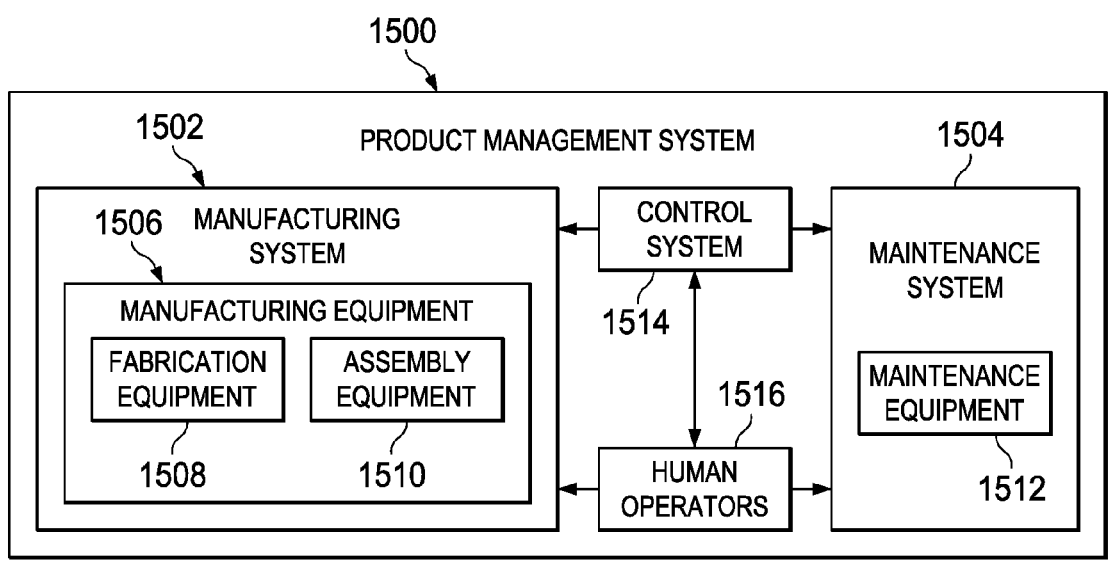
FIG. 15 is an illustration of a block diagram of a product management system in accordance with an illustrative embodiment.

Turning now to FIG. 15, an illustration of a block diagram of a product management system is depicted in accordance with an illustrative embodiment. Product management system 1500 is a physical hardware system. In this illustrative example, product management system 1500 may include at least one of manufacturing system 1502 or maintenance system 1504.

Manufacturing system 1502 is configured to manufacture products, such as aircraft 1400 in FIG. 14. As depicted, manufacturing system 1502 includes manufacturing equipment 1506. Manufacturing equipment 1506 includes at least one of fabrication equipment 1508 or assembly equipment 1510.

Fabrication equipment 1408 is equipment that may be used to fabricate components for parts used to form aircraft 1400. For example, fabrication equipment 1408 may include machines and tools. These machines and tools may be at least one of a drill, a hydraulic press, a furnace, a mold, a composite tape laying machine, a vacuum system, a lathe, or other suitable types of equipment. Fabrication equipment 1508 may be used to fabricate at least one of metal parts, composite parts, semiconductors, circuits, fasteners, ribs, skin panels, spars, antennas, or other suitable types of parts.

Assembly equipment 1510 is equipment used to assemble parts to form aircraft 1400. In particular, assembly equipment 1510 may be used to assemble components and parts to form aircraft 1400. Assembly equipment 1510 also may include machines and tools. These machines and tools may be at least one of a robotic arm, a crawler, a faster installation system, a rail-based drilling system, or a robot. Assembly equipment 1510 may be used to assemble parts such as seats, horizontal stabilizers, wings, engines, engine housings, landing gear systems, and other parts for aircraft 1400.

In this illustrative example, maintenance system 1504 includes maintenance equipment 1512. Maintenance equipment 1512 may include any equipment needed to perform maintenance on aircraft 1400. Maintenance equipment 1512 may include tools for performing different operations on parts on aircraft 1400. These operations may include at least one of disassembling parts, refurbishing parts, inspecting parts, reworking parts, manufacturing replacement parts, or other operations for performing maintenance on aircraft 1400. These operations may be for routine maintenance, inspections, upgrades, refurbishment, or other types of maintenance operations.

In the illustrative example, maintenance equipment 1512 may include ultrasonic inspection devices, x-ray imaging systems, vision systems, drills, crawlers, and other suitable device. In some cases, maintenance equipment 1512 may include fabrication equipment 1508, assembly equipment 1510, or both to produce and assemble parts that may be needed for maintenance.

Product management system 1500 also includes control system 1514. Control system 1514 is a hardware system and may also include software or other types of components. Control system 1514 is configured to control the operation of at least one of manufacturing system 1502 or maintenance system 1504. In particular, control system 1514 may control the operation of at least one of fabrication equipment 1508, assembly equipment 1510, or maintenance equipment 1512.

The hardware in control system 1514 may be using hardware that may include computers, circuits, networks, and other types of equipment. The control may take the form of direct control of manufacturing equipment 1506. For example, robots, computer-controlled machines, and other equipment may be controlled by control system 1514. In other illustrative examples, control system 1514 may manage operations performed by human operators 1516 in manufacturing or performing maintenance on aircraft 1400 in FIG. 14. For example, control system 1514 may assign tasks, provide instructions, display models, or perform other operations to manage operations performed by human operators 1516. In these illustrative examples, corrosion risk analysis system 108 may be implemented in control system 1514 to manage at least one of the manufacturing or maintenance of aircraft 1400 in FIG. 14.

For example, corrosion risk analysis system 108 in FIG. 1 may be used to identify corrosion risks for parts or other components being manufactured for use in manufacturing or maintenance. With the identification of the corrosion risks, changes to the designs for parts or other components in a vehicle may be made to reduce the corrosion risks. These changes may be made in a model of vehicle 106 in FIG. 1. With an updated model, control system 1514 may control the manufacturing of a vehicle or parts for the vehicle for use in maintenance.

In the different illustrative examples, human operators 1516 may operate or interact with at least one of manufacturing equipment 1506, maintenance equipment 1512, or control system 1514. This interaction may be performed to manufacture aircraft 1400 in FIG. 14.

Of course, product management system 1500 may be configured to manage other products other than aircraft 1400. Although product management system 1500 has been described with respect to manufacturing in the aerospace industry, product management system 1500 may be configured to manage products for other industries. For example, product management system 1500 may be configured to manufacture products for the automotive industry as well as any other suitable industries.

In one illustrative example, one or more technical solutions are present that overcome a technical problem with identifying corrosion risks for aircraft and other vehicles. Thus, the different illustrative examples provide one or more technical solutions with a technical effect of allowing for the identification of corrosion risks and, in particular, aggregated corrosion risks earlier in the process of manufacturing a vehicle. Further, this detection of the corrosion risks may be used during different times in the life cycle of a vehicle, such as an aircraft. For example, parts may be designed or redesigned for the aircraft for use during maintenance. The maintenance may be part of normal maintenance to replace parts, upgrades, refurbishments, or other types of maintenance. Changes to the design of the parts during the maintenance may be made to reduce the corrosion risks which may reduce the amount and frequency of maintenance needed.

For example, with the identification of at least one of corrosion risks and aggregated corrosion risks, these risks may be used to select materials. For example, two metals may be available for use in a structure and the two metals may have the same corrosion risk. As a result, other factors of the two metals such as cost, weight, availability, or other factors may be used to select the metal. Thus, identifying at least one of the corrosion risks and the aggregated corrosion risks may be used to perform operations such as making changes based on cost or strength that is present due to changes that reduce the corrosion risks.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    A display system;
    an extractor configured to identify potential corrosion surfaces for a vehicle using a model for the vehicle;
    a corrosion predictor configured to predict corrosion risks for the potential corrosion surfaces using a group of sources identifying corrosion risks for different types of materials; and an aggregator configured to aggregate the corrosion risks predicted for a group of potential corrosion surfaces into a group of aggregated corrosion risks for a group of functional design units in the vehicle to identify a corrosion risk in the vehicle from the group of aggregated corrosion risks, and to enable a change in the model to reduce the identified corrosion risk;
    a risk analyzer configured to generate a corrosion risk assessment for the vehicle using the group of aggregated corrosion risks for the group of functional design units, wherein the corrosion risk assessment for the vehicle is feedback for changes to the model for the vehicle; and
    a graphical user interface configured to display the corrosion risk assessment on the display system to a user and allow the user to change the model for the vehicle to reduce the corrosion risks.

2. The apparatus of claim 1, wherein the corrosion risk assessment comprises at least one of the group of aggregated corrosion risks, an identification of each of the group of aggregated corrosion risks that is greater than a selected threshold risk, or suggested changes to the model that reduce the group of aggregated corrosion risks.

3. The apparatus of claim 1, wherein the corrosion risk assessment for the vehicle takes into account an impact to a group of design factors for the vehicle.

4. The apparatus of claim 3, wherein the group of design factors is selected from at least one of corrosion, strength, lift, cost, aerodynamic performance, or manufacturability.

5. The apparatus of claim 1, wherein the risk analyzer is configured to display a view of the model for the vehicle in the graphical user interface with graphical indicators on a display system, wherein the graphical indicators indicate the group of aggregated corrosion risks on the group of functional design units displayed in the view of the model for the vehicle.

6. The apparatus of claim 1, wherein in identifying the potential corrosion surfaces for the vehicle using the model, the extractor identifies material contacts for surfaces for components in the model for the vehicle and identifies potential corrosion contacts in the model using the material contacts and materials present in the components at the material contacts.

7. The apparatus of claim 6, wherein the components are selected from at least one of a part, an assembly, a coating, an adhesive, a fastener, a washer, or a clip.

8. The apparatus of claim 1, wherein a functional design unit in the group of functional design units is selected from one of a part, an assembly, and a system in the vehicle.

9. The apparatus of claim 1, wherein the corrosion risks are selected from at least one of a uniform corrosion, an atmospheric corrosion, an intergranular corrosion, a stress-induced corrosion, a stress-corrosion cracking, a crevice corrosion, a galvanic corrosion, a pitting corrosion, a localized corrosion, a selective leaching, an erosion corrosion, and a microbial corrosion.

10. The apparatus of claim 1, wherein the potential corrosion surfaces are selected from at least one of an environmental surface that contacts an environment or a contact surface that contacts a material.

11. The apparatus of claim 1, wherein the vehicle is selected from one of a mobile platform, an aircraft, a surface ship, a tank, a personnel carrier, a train, a spacecraft, a satellite, a rocket, a submarine, a bus, and an automobile.

12. A corrosion risk analysis system comprising:
    a display system;
    an extractor configured to identify material contacts between components in a model for a vehicle during a design phase of the vehicle and identifies potential corrosion contacts for the vehicle using the material contacts and materials present in structures at the material contacts;
    a corrosion predictor configured to predict corrosion risks for the potential corrosion contacts accessing a group of sources identifying corrosion risks for different types of materials;
    an aggregator configured to aggregate the corrosion risks predicted for the group of potential corrosion contacts into a group of aggregated corrosion risks for a group of functional design units in the vehicle;
    a risk analyzer configured to generate a corrosion risk assessment for the vehicle using the group of aggregated corrosion risks for the group of functional design units to identify a corrosion risk in the vehicle from the group of aggregated corrosion risks, and to enable a change in the model to reduce the identified corrosion risk, wherein the corrosion risk assessment for the vehicle is feedback for using in making changes to the model for the vehicle during the design phase of the vehicle; and a graphical user interface configured to display the corrosion risk assessment on the display system to a user and allow the user to change the model for the vehicle to reduce the corrosion risks.

13. The corrosion risk analysis system of claim 12, wherein the corrosion risk assessment for the vehicle takes into account an impact to a group of design factors for the vehicle.

14. The corrosion risk analysis system of claim 13, wherein the group of design factors is selected from at least one of corrosion, strength, lift, cost, aerodynamic performance, or manufacturability.

15. The corrosion risk analysis system of claim 14, wherein a functional design unit in the group of functional design units is selected from one of a part, an assembly, and a system in the vehicle.

16. The corrosion risk analysis system of claim 14, wherein the components are selected from at least one of a part, a coating, an adhesive, a fastener, a washer, or a clip.

17. A method for analyzing potential corrosion for a vehicle, the method comprising:
   identifying potential corrosion surfaces for the vehicle using a model for the vehicle;
   predicting corrosion risks for each of the potential corrosion surfaces;
   aggregating the corrosion risks predicted into a group of aggregated corrosion risks for a group of functional design units for the vehicle;
   generating a corrosion risk assessment for the vehicle to identify a corrosion risk in the vehicle from the group of aggregated corrosion risks, and to enable a change in the model to reduce the identified corrosion risk, wherein the corrosion risk assessment for the vehicle is feedback for changes to the model of the vehicle; and
   changing the model of the vehicle in accordance with the risk assessment to reduce the corrosion risks.

18. The method of claim 17 further comprising:
   generating the corrosion risk assessment for the vehicle using the group of aggregated corrosion risks for the group of functional design units.

19. The method of claim 18, wherein the corrosion risk assessment comprises at least one of the group of aggregated corrosion risks, an identification of each of the group of aggregated corrosion risks that is greater than a selected threshold risk, or suggested changes to the model that reduce the group of aggregated corrosion risks.

20. The method of claim 18, wherein the corrosion risk assessment for the vehicle takes into account an impact to a group of design factors for the vehicle.

21. The method of claim 20, wherein the group of design factors is selected from at least one of corrosion, strength, lift, cost, aerodynamic performance, or manufacturability.

22. The method of claim 18 further comprising:
   displaying the model for the vehicle with graphical indicators on a display system, wherein the graphical indicators indicate the group of aggregated corrosion risks on the group of functional design units displayed in the model for the vehicle.

23. The method of claim 17, wherein in identifying the potential corrosion surfaces for the vehicle using the model comprises:
   identifying material contacts for surfaces for components in the model for the vehicle; and
   identifying potential corrosion contacts using the material contacts and materials present in components at the material contacts in the model.

24. The method of claim 23, wherein components are selected from at least one of a part, a coating, an adhesive, a fastener, a washer, or a clip.

25. The method of claim 17, wherein a functional design unit in the group of functional design units is selected from one of a part, an assembly, and a system in the vehicle.

26. The method of claim 17, wherein the corrosion risks are selected from at least one of a uniform corrosion, an atmospheric corrosion, an intergranular corrosion, a stress-induced corrosion, a stress-corrosion cracking, a crevice corrosion, a galvanic corrosion, a pitting corrosion, a localized corrosion, a selective leaching, an erosion corrosion, and a microbial corrosion.

27. The method of claim 17, wherein the potential corrosion surfaces are selected from at least one of an environmental surface that contacts an environment or a contact surface that contacts a material.

28. The method of claim 17, wherein the vehicle is selected from one of a mobile platform, an aircraft, a surface ship, a tank, a personnel carrier, a train, a spacecraft, a satellite, a rocket, a submarine, a bus, and an automobile.

* * * * *